United States Patent
Yen et al.

(10) Patent No.: US 9,675,423 B2
(45) Date of Patent: Jun. 13, 2017

(54) ULTRASOUND ENERGY BARRIER FOR AVOIDING ENERGY ACCUMULATION IN BONE REGION DURING TUMOR TREATMENT

(71) Applicant: National Taiwan University, Taipei (TW)

(72) Inventors: Jia-yush Yen, Taipei (TW); Yu-tin Chao, Taipei (TW); Ya-lin Yu, Taipei (TW); Che-jung Hsu, Taipei (TW); Yung-yaw Chen, Taipei (TW); Ming-chih Ho, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 600 days.

(21) Appl. No.: 13/914,704

(22) Filed: Jun. 11, 2013

(65) Prior Publication Data

US 2014/0364776 A1    Dec. 11, 2014

(51) Int. Cl.
  *A61B 8/00*   (2006.01)
  *A61N 7/02*   (2006.01)
  *A61B 90/00*  (2016.01)

(52) U.S. Cl.
  CPC ...... *A61B 90/04* (2016.02); *A61B 2090/0454* (2016.02); *A61B 2090/0472* (2016.02)

(58) Field of Classification Search
  None
  See application file for complete search history.

(56) References Cited

U.S. PATENT DOCUMENTS

| 3,937,971 A * | 2/1976 | Morrison | A61B 6/107 250/515.1 |
| 3,950,651 A * | 4/1976 | Flocee | A61B 6/06 378/147 |
| 4,622,969 A * | 11/1986 | Forssmann | G10K 11/002 601/4 |
| 4,655,205 A * | 4/1987 | Hepp | A61B 17/2251 128/846 |
| 2013/0131494 A1* | 5/2013 | Salomir | A61N 7/02 600/411 |

OTHER PUBLICATIONS

Printout of http://biology.tutorvista.com/organism/kingdom-animalia.html dated Oct. 27, 2015.*
Printout of http://animaldiversity.org/accounts/Animalia/ dated Oct. 27, 2015.*

* cited by examiner

*Primary Examiner* — Long V Le
*Assistant Examiner* — Bradley Impink
(74) *Attorney, Agent, or Firm* — Hamre, Schumann, Mueller & Larson, P.C.

(57) ABSTRACT

An ultrasound energy barrier for avoiding energy accumulation in a to-be-protected region during tumor treatment has a barrier element and a positioning element. The barrier element is attached to a body surface of an animal outside a to-be-protected region and a to-be-treated tumor in turn, the barrier element has an outline matched with the to-be-protected region to thus shield the to-be-protected region, so as to avoid energy accumulation in the to-be-protected region during an ultrasound focusing treatment of the to-be-treated tumor. The positioning element positioning the barrier element on the body surface during the ultrasound focusing treatment.

11 Claims, 7 Drawing Sheets

ULTRASOUND ENERGY BARRIER FOR AVOIDING ENERGY ACCUMULATION IN BONE REGION DURING TUMOR TREATMENT

FIELD OF THE INVENTION

The present invention relates to an ultrasound energy barrier for avoiding energy accumulation in a to-be-protected region during tumor treatment, and more particularly to an ultrasound energy barrier for avoiding energy accumulation in a to-be-protected region during tumor treatment by using high-intensity focused ultrasound (HIFU).

BACKGROUND OF THE INVENTION

One approach to treating a diseased tissue, such as a cancerous tumor, is surgical removal. However, surgical removal is invasive, and may be complicated and time consuming. Additionally, surgical treatment requires the selective treatment for each type of diseased tissues. Surgical treatment can also result in serious complications, such as from anesthesia. Clearly, a more comprehensive and non-invasive treatment of similar or better efficacy than surgical removal is desirable.

For example, high-intensity focused ultrasound (HIFU) has been demonstrated to be a safe modality to treat diseased tissue noninvasively. For example, HIFU has been used to treat liver cancer, ovary cancer, prostrate cancer, kidney cancer and testicular cancer. A HIFU system has an ultrasound transducer to transmit ultrasound waves which pass through the body skin of an animal and are focused on a to-be-treated tissue, such as a liver tumor. The incident focused ultrasound waves are absorbed and converted into heat at the focal point, known as the biological focal region (BFR), resulting in thermal ablation of the tumor cells. The high intensity ultrasound waves also further cause the tissue bubbles to oscillate steadily resulting in shear stresses that cause tumor cell damage, this is known as "stable cavitation". The above-mentioned certain pressure threshold bubbles explode vigorously resulting in localized high acoustic pressure that causes tumor tissue damage, this is known as "inertial cavitation".

However, although the transmitting power of the therapeutic transducer can be increased to improve the therapeutic efficiency, the normal tissue along the pathway of the ultrasound transmission is more likely to be burned in a high-intensity ultrasound environment. In addition, at present, when the HIFU technique is clinically applied to a hepatic tumor, the hepatic tumor is blocked by the ribs in the pathway of the ultrasound transmission, and the ultrasound transmission will heat and burn the rib tissue to cause damage of the ribs. Thus, before the therapy of HIFU, it is suggested to surgically remove the ribs in advance, in order to increase the energy deposition at the target location, shorten the treatment time and improve therapeutic effects. As a result, the noninvasiveness of HIFU treatment cannot be ensured, which is undesirable for the patients and doctors.

The above-mentioned problems have disadvantageously limited the use of the HIFU treatment as a technique for clinical practice. Therefore, the technical problems with respect to increasing the energy deposition at target location, effectively treating the deep-seated tumors without damaging the surrounding normal tissue (such as ribs) in the acoustic pathway, and treating a hepatic tumor that is blocked by the ribs without surgical removal of the ribs, need to be solved urgently.

It is therefore tried by the inventor to develop an ultrasound energy barrier for avoiding energy accumulation in a to-be-protected region during tumor treatment to solve the problems existing in the conventional HIFU treatment, as described above.

SUMMARY OF THE INVENTION

A primary object of the present invention is to provide an ultrasound energy barrier for avoiding energy accumulation in a to-be-protected region during tumor treatment, which has a barrier element having an outline matched with the to-be-protected region for shielding the to-be-protected region, so as to reflect or absorb ultrasound waves/energy and thus avoid energy accumulation in the to-be-protected region during an ultrasound focusing treatment of a to-be-treated tumor.

A secondary object of the present invention is to provide an ultrasound energy barrier for avoiding energy accumulation in a to-be-protected region during tumor treatment, wherein the thickness of the barrier element along a transmission direction of the ultrasound waves is designed to cause that the barrier element has a transmission coefficient equal to 1. Thus, the barrier element can block a portion of the ultrasound waves to protect ribs from being heated and burned, while other portion of the ultrasound waves still can transmit and pass through a space between each two of adjacent barrier elements to be focused on a hepatic tumor behind the ribs.

A third object of the present invention is to provide an ultrasound energy barrier for avoiding energy accumulation in a to-be-protected region during tumor treatment, wherein the barrier element is made of plastic deformation material or elastic deformation material, so that the barrier element can be temporarily, permanently or elastically deformed to have a curved configuration which is advantageous to substantially match with a profile of the body surface of the animal.

A fourth object of the present invention is to provide an ultrasound energy barrier for avoiding energy accumulation in a to-be-protected region during tumor treatment, which has a positioning element, such as an adhesive layer, a tightening belt or an elastic band, which is used to position the barrier element on the body surface during the ultrasound focusing treatment, wherein the adhesive layer is made of thermal insulation material to protect the body surface from being burned by heat from the barrier element.

To achieve the above object, the present invention provides an ultrasound energy barrier for avoiding energy accumulation in a to-be-protected region during tumor treatment which comprises:

a barrier element attached to a body surface of an animal outside a to-be-protected region and a to-be-treated tumor in turn, wherein the barrier element has an outline matched with the to-be-protected region to thus shield the to-be-protected region, so as to avoid energy accumulation in the to-be-protected region during an ultrasound focusing treatment of the to-be-treated tumor; and a positioning element positioning the barrier element on the body surface during the ultrasound focusing treatment.

In one embodiment of the present invention, the barrier element is an ultrasound reflection plate to reflect ultrasound waves transmitted from an ultrasound probe during the ultrasound focusing treatment.

In one embodiment of the present invention, the barrier element is an ultrasound absorption plate to absorb ultrasound waves transmitted from an ultrasound probe during the ultrasound focusing treatment.

In one embodiment of the present invention, the barrier element comprises: an ultrasound reflection plate and an ultrasound absorption plate to reflect and absorb the ultrasound waves transmitted from an ultrasound probe during the ultrasound focusing treatment, respectively, wherein the ultrasound absorption plate is connection to the ultrasound reflection plate and relatively close to the ultrasound probe.

In one embodiment of the present invention, the barrier element is a tubular reactive muffler which comprises an outer ultrasound reflection plate and an inner ultrasound absorption plate to reflect and absorb the ultrasound waves transmitted from an ultrasound probe during the ultrasound focusing treatment, respectively.

In one embodiment of the present invention, the tubular reactive muffler further comprises an opening, a channel and a resonance cavity in turn, and the resonance cavity is communicated with the channel to attenuate the ultrasound waves. An extension direction of the opening, the channel and the resonance cavity is parallel to (or perpendicular to) a transmission direction of the ultrasound waves.

In one embodiment of the present invention, the barrier element is at least one tubular acoustic filter, each of which comprises an outer ultrasound reflection plate and an inner ultrasound absorption plate to reflect and absorb the ultrasound waves transmitted from an ultrasound probe during the ultrasound focusing treatment, respectively.

In one embodiment of the present invention, the tubular acoustic filter further comprises a first opening, a channel and a second opening in turn, and a middle portion of the channel has a middle expanded chamber to attenuate the ultrasound waves. An extension direction of the first opening, the channel and the second opening is parallel to (or perpendicular to) a transmission direction of the ultrasound waves.

In one embodiment of the present invention, the thickness of the barrier element along a transmission direction of the ultrasound waves is a value, in which the barrier element has a transmission coefficient equal to 1.

In one embodiment of the present invention, the thickness of the barrier element is calculated by an equation, as follows: T=1.5 mm×N/M when the frequency of the ultrasound waves is 0.5 MHz×M, wherein T is the thickness of the barrier element, N is a positive integer ranged from 1 to 10, and M is a positive number ranged from 1 to 10.

In one embodiment of the present invention, the barrier element is made of plastic deformation material or elastic deformation material, so that the barrier element is deformed to match with a profile of the body surface.

In one embodiment of the present invention, the positioning element is an adhesive layer which is made of thermal insulation material and adhered to a surface of the barrier element relatively close to the body surface.

In one embodiment of the present invention, the positioning element is a tightening belt or an elastic band, which is made of thermal insulation material and has two tying ends tied on two ends of the barrier element.

In one embodiment of the present invention, the barrier element has an outline matched with a bone, such as a rib.

In one embodiment of the present invention, the ultrasound focusing treatment is high-intensity focused ultrasound (HIFU), wherein the frequency of the ultrasound waves is 0.5-5 MHz, wherein the frequency of ultrasound waves transmitted from an ultrasound probe is 0.5-5 MHz.

In one embodiment of the present invention, the ultrasound absorption plate is made of ultrasound absorption material, wherein a perforation rate of pores or perforation holes in the ultrasound absorption material is 0.05-0.6, and the diameter of the pores or perforation holes is smaller than ½ of the wavelength of the ultrasound waves.

Furthermore, the present invention provides another ultrasound energy barrier for avoiding energy accumulation in a to-be-protected region during tumor treatment which comprises:

a barrier element attached to a body surface of an animal outside a to-be-protected region and a to-be-treated tumor in turn, wherein the barrier element has an outline matched with the to-be-protected region to thus shield the to-be-protected region, so as to avoid energy accumulation in the to-be-protected region during an ultrasound focusing treatment of the to-be-treated tumor.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, and etc., are only directions by referring to the accompanying drawings, and thus the used directional terms are used to describe and understand the present invention, but the present invention is not limited thereto.

Figure 1:
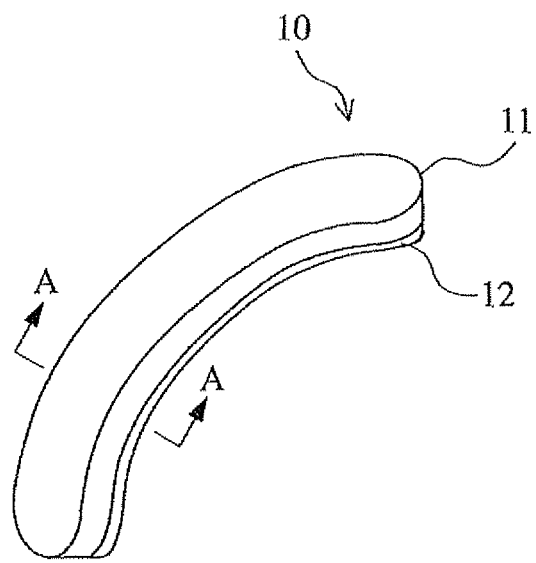
FIG. 1 is a perspective view of an ultrasound energy barrier according to a first embodiment of the present invention.
Figure 2A:
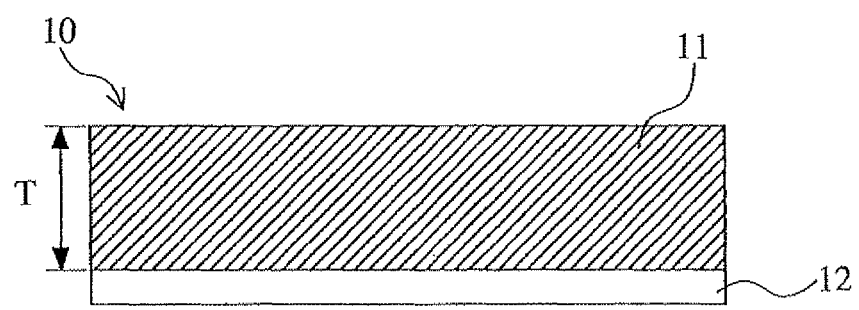
FIG. 2A is a transverse cross-sectional view of the ultrasound energy barrier along a line A-A of FIG. 1.

Referring now to FIGS. 1 and 2A, an ultrasound energy barrier for avoiding energy accumulation in a to-be-protected region during tumor treatment according to a first embodiment of the present invention is illustrated. As shown, an ultrasound energy barrier 10 comprises a barrier element and a positioning element. In the embodiment, the barrier element is an ultrasound reflection plate 11, and the positioning element is an adhesive layer 12. The ultrasound reflection plate 11 is used to reflect ultrasound waves transmitted from an ultrasound probe during the ultrasound focusing treatment. The ultrasound reflection plate 11 is made of ultrasound reflection material, such as metal, plastic, glass, glass fiber, wherein the metal can be stainless steel, titanium or titanium alloy; the plastic can be polyvinyl chloride (PVC), but not limited thereto. The ultrasound reflection plate 11 can be attached to a body surface of an animal outside a to-be-protected region and a to-be-treated tumor in turn, wherein the ultrasound reflection plate 11 has an outline matched with the to-be-protected region to thus shield the to-be-protected region, so as to avoid energy accumulation in the to-be-protected region during an ultrasound focusing treatment of the to-be-treated tumor.

Furthermore, the adhesive layer 12 is preferably made of thermal insulation material, such as various economically available thermal-insulation adhesive material, especially waterproof thermal-insulation adhesive material, such as a thermal-tape made of acrylic polymer, silicone elastomer filled with ceramic particles, thermosetting adhesive filled with boron nitride particles, and the like, but not limited thereto. The adhesive layer 12 does not absorb ultrasound waves and can bear at least 65-100° C. A front surface of the adhesive layer 12 is adhered to a rear surface of the ultrasound reflection plate 11 relatively close to the body surface of the animal. A rear surface of the adhesive layer 12 is combined with a release film (not-shown) before use, and the rear surface of the adhesive layer 12 is used to adhere to the body surface when starting to execute the ultrasound focusing treatment of the to-be-treated tumor. The adhesive layer 12 made of thermal insulation material also can be used to protect the body surface from being burned by heat from the barrier element after reflecting or absorbing the ultrasound waves.

Figure 2B:
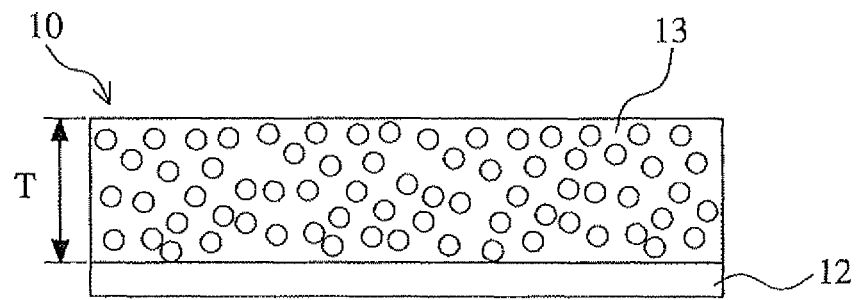
FIG. 2B is a transverse cross-sectional view of an ultrasound energy barrier according to a second embodiment of the present invention, similar to FIG. 2A.

Referring to FIG. 2B, in a second embodiment of the present invention, the barrier element of the ultrasound energy barrier 10 can be replaced by an ultrasound absorption plate 13, while the positioning element is still an adhesive layer 12. The ultrasound absorption plate 13 is used to absorb ultrasound waves transmitted from an ultrasound probe during the ultrasound focusing treatment. The ultrasound absorption plate 13 is made of ultrasound absorption material, such as synthetic foam material, sponge or porous rubber or perforation plate, but not limited thereto, wherein the perforation rate of pores or perforation holes in the ultrasound absorption material is preferably 0.05-0.6, such as 0.1, 0.2, 0.3, 0.4 or 0.5, while the diameter of the pores or the perforation holes is preferably smaller than ½ of the wavelength of the ultrasound waves, such as ⅓, ¼, ⅕, ⅙ and so on. The ultrasound absorption plate 13 can be attached to a body surface of an animal outside a to-be-protected region and a to-be-treated tumor in turn, wherein the ultrasound absorption plate 13 has an outline matched with the to-be-protected region to thus shield the to-be-protected region, so as to avoid energy accumulation in the to-be-protected region during an ultrasound focusing treatment of the to-be-treated tumor. The adhesive layer 12 is also made of thermal insulation material, and used to adhere the ultrasound absorption plate 13 to the body surface of the animal.

Figure 2C:
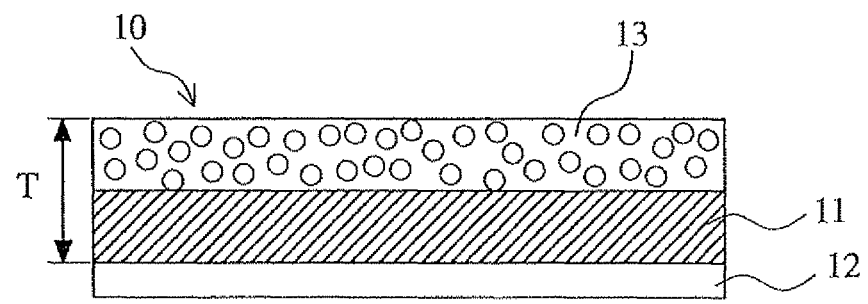
FIG. 2C is a transverse cross-sectional view of an ultrasound energy barrier according to a third embodiment of the present invention, similar to FIGS. 2A and 2B.

Referring to FIG. 2C, in a third embodiment of the present invention, the barrier element of the ultrasound energy barrier 10 can comprise an ultrasound reflection plate 11 and an ultrasound absorption plate 13, while the positioning element is still an adhesive layer 12, wherein the ultrasound reflection plate 11 is sandwiched between the ultrasound absorption plate 13 and the adhesive layer 12. Alternatively, the ultrasound absorption plate 13 is sandwiched between the ultrasound reflection plate 11 and the adhesive layer 12. The function of all layers is substantially the same as that of the first and second embodiments, and thus the detailed description thereof is omitted.

In the first, second or third embodiment of the present invention, the ultrasound reflection material and/or ultrasound absorption material of the barrier element is preferably plastic deformation material or elastic deformation material, so that the barrier element can be temporarily, permanently or elastically deformed to have a curved configuration which is advantageous to substantially match with a profile of the body surface of the animal.

Figure 3:
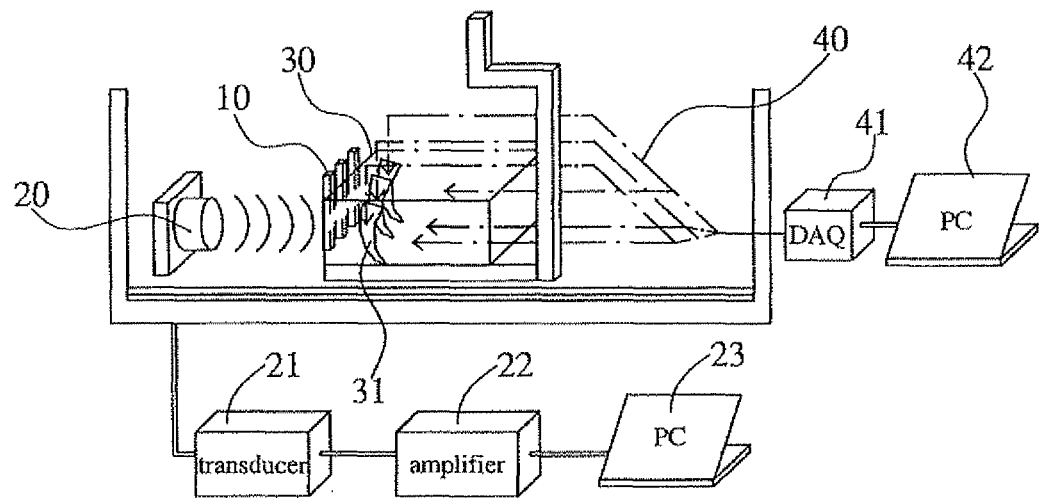
FIG. 3 is a schematic view of the ultrasound energy barrier for simulating a tumor treatment of HIFU according to the third embodiment of the present invention.

Referring now to FIG. 3, a schematic view of the ultrasound energy barrier for simulating a tumor treatment of high-intensity focused ultrasound (HIFU) according to the third embodiment of the present invention is illustrated, wherein an ultrasound probe 20, a biological phantom 30 and a plurality of thermocouple units 40 are used. The ultrasound probe 20 is electrically connected to an ultrasound transducer 21, a signal amplifier 22 and a computer 23 (such as a personal computer) in turn, wherein the computer 23 is used to control and send a signal to the signal amplifier 22 which amplifies the signal to the ultrasound transducer 21, and then the ultrasound transducer 21 generates ultrasound waves which are transmitted toward the biological phantom 30 through the ultrasound probe 20. The biological phantom 30 can be made by using animal protein, and a plurality of ribs 31 (such as three pig ribs) are inserted into the biological phantom 30, so as to simulate a body tissue of an animal (such as a human).

Furthermore, the thermocouple units 40 are a plurality of probes electrically connected to a data acquisition unit 41 (DAQ) and a computer 42 in turn, wherein the thermocouple units 40 are used to detect temperature variation, the data acquisition unit 41 is used to collect the data of temperature variation; and the computer 42 is used to process and store the data. The thermocouple units 40 are vertically inserted into a rear surface of the biological phantom 30 based on a plurality of fixed insertion depths and arranged in an array manner, respectively, so as to construct a plurality of internal 2D planes to commonly build up a thermal detection field for detecting the temperature variation in the biological phantom 30 behind the ribs 31. For example, 5×5 of the thermocouple units 40 construct a 2D plane, and there are five 2D planes in five different fixed insertion depths, i.e. totally, 5×5×5 of the thermocouple units 40 construct a thermal detection field in the biological phantom 30. Meanwhile, a portion of the thermocouple units 40 (such as three of the thermocouple units 40) are inserted into a top surface of the biological phantom 30 and in contact with the front surface of each of the ribs 31 (such as three ribs 31) for detecting the temperature variation of each of the ribs 31.

Moreover, a plurality of ultrasound energy barriers 10 (such as the ultrasound energy barriers 10 as shown in FIG. 2C) can be side-by-side attached to a front surface of the biological phantom 30 outside the ribs 31 and the thermal detection field of the thermocouple units 40, wherein each of the ultrasound energy barriers 10 has an outline matched with the ribs 31 to thus shield the ribs 31, so as to avoid energy accumulation in the ribs 31 during a simulation experiment of high-intensity focused ultrasound (HIFU) of the biological phantom 30. All of the ultrasound energy barriers 10, the ultrasound probe 20, the biological phantom 30 and the thermocouple units 40 are immersed in water within a container, wherein the combination of the ultrasound energy barriers 10, the ultrasound probe 20, the biological phantom 30 and the thermocouple units 40 are supported by a holder structure.

Figure 4:
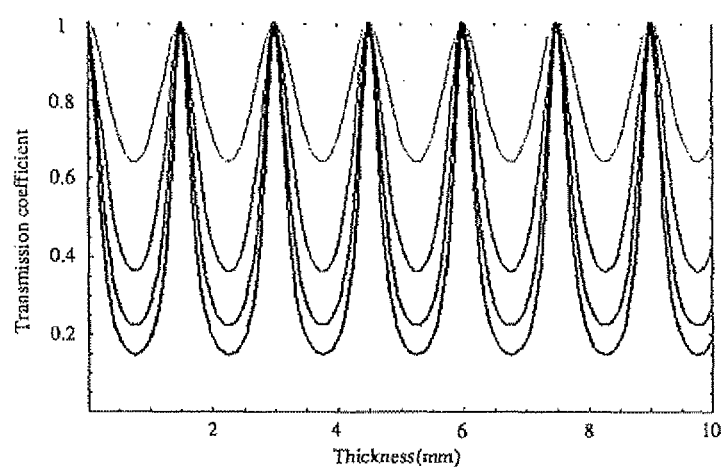
FIG. 4 is a curve diagram of the transmission coefficient and the thickness of the ultrasound energy barrier based on simulation data of FIG. 3.

Referring to FIG. 4, a curve diagram of the transmission coefficient and the thickness of the ultrasound energy barrier based on simulation data of FIG. 3 is illustrated, wherein the frequency of ultrasound waves transmitted from a NFU ultrasound probe is 0.5 MHz to 5.0 MHz, the thickness (T) of the ultrasound energy barriers 10 (mainly means the barrier element) along a transmission direction of the ultrasound waves is 0.5 mm to 10 mm. It should be noted that, when the thickness (T) of the barriers element along a transmission direction of the ultrasound waves is 1.5 mm, 3 mm, 4.5 mm, 6 mm, 7.5 mm and 9 mm (i.e. 1.5×N), the barrier element has a transmission coefficient equal to 1, regardless of what kind of material and cross-sectional shape of the barrier element; in other words, when the thickness (T) of the barrier element along a transmission direction of the ultrasound waves is designed to cause that the barrier element has a transmission coefficient equal to 1, the barrier element can block a portion of the ultrasound waves by reflection or absorption, to protect the ribs 31 from being heated and burned, while other portion of the ultrasound waves still can transmit and pass through a space between each two of adjacent barrier elements (and a space between each two of adjacent ribs 31) to be focused on a to-be-treated tumor behind the ribs 31.

Briefly, the thickness of the barrier element is calculated by an equation, as follows: T=1.5 mm×N/M when the frequency of the ultrasound waves is 0.5 MHz×M, wherein T is the thickness of the barrier element, N is a positive integer ranged from 1 to 10, and M is a positive number ranged from 1 to 10. For example, the thickness (T) of the barrier element can be 1.5 mm, 3 mm, 4.5 mm, 6 mm, 7.5 mm or 9 mm when frequency of the ultrasound waves is 0.5 MHz (i.e. M=1); the thickness (T) of the barrier element can be 0.75 mm, 1.5 mm, 2.25 mm, 3 mm, 3.75 mm or 4.5 mm when frequency of the ultrasound waves is 1.0 MHz (i.e. M=2).

Figure 5:
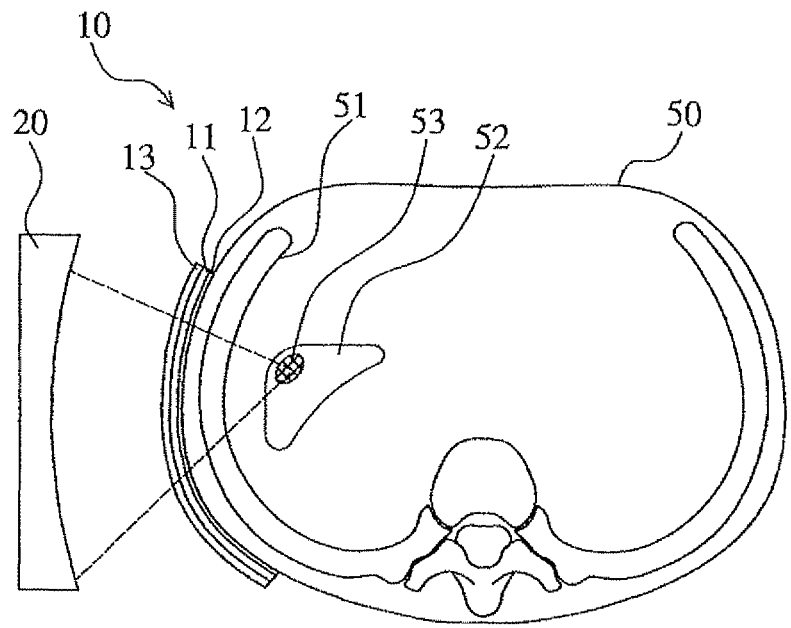
FIG. 5 is an operational view of the ultrasound energy barrier for avoiding energy accumulation in a bone region during tumor treatment according to the third preferred embodiment of the present invention.

Referring to FIG. 5, an operational view of the ultrasound energy barrier for avoiding energy accumulation in a bone region during tumor treatment according to the third preferred embodiment of the present invention is illustrated, wherein an operational method of the ultrasound energy barrier comprises the following steps: in a first step, providing a plurality of ultrasound energy barriers 10 (such as the ultrasound energy barrier 10 as shown in FIG. 2C) which are side-by-side attached to a body surface of an animal 50 (such as a human) outside a plurality of to-be-protected region (such as ribs 51 or other bones) and a to-be-treated tumor (such as hepatic tumor 53 within a liver 52) in turn, wherein the ultrasound energy barriers 10 has an outline matched with the ribs 51 to thus shield the ribs 51. In a second step, providing an ultrasound probe 20 of a high-intensity focused ultrasound (HIFU) machine to emit ultrasound waves which are transmitted toward the to-be-protected region (i.e. the ribs 51) and the to-be-treated tumor (i.e. the hepatic tumor 53), wherein the barrier element of the ultrasound energy barriers 10 can reflect or absorb the ultrasound waves, so as to avoid energy accumulation in the ribs 51 during the high-intensity focused ultrasound (HIFU) treatment of the hepatic tumor 53. At this time, if the thickness (T) of the barrier element (such as the total thickness of the ultrasound reflection plate 11 and the ultrasound absorption plate 13 as shown in FIG. 2C) along a transmission direction of the ultrasound waves is designed to cause that the barrier element has a transmission coefficient equal to 1, the barrier element can block a portion of the ultrasound waves to protect the ribs 51 from being heated and burned, while other portion of the ultrasound waves still can transmit and pass through a space between each two of adjacent barrier elements (and a space between each two of adjacent ribs 51) to be focused on the hepatic tumor 53 behind the ribs 51.

Figure 6:
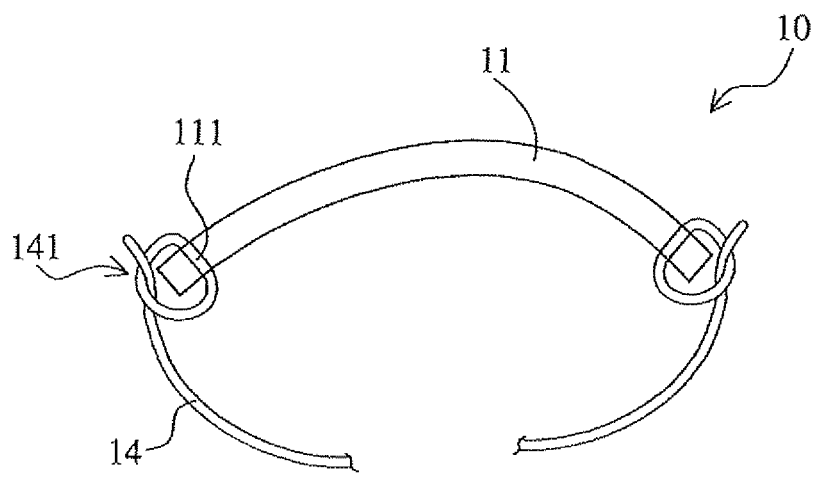
FIG. 6 is a longitudinal cross-sectional view of an ultrasound energy barrier according to a fourth embodiment of the present invention.

Referring now to FIG. 6, a longitudinal cross-sectional view of an ultrasound energy barrier according to a fourth embodiment of the present invention is illustrated and similar to the first embodiment, so that the fourth embodiment uses similar terms or numerals of the first embodiment. As shown, the difference of the fourth embodiment is that the ultrasound energy barrier 10 comprises: a barrier element and a positioning element, wherein the barrier element can be an ultrasound reflection plate 11, an ultrasound absorption plate 13 or the combination thereof; and the positioning element is a tightening belt 14 (or an elastic band), which is made of thermal insulation material and has two tying ends 141 tied on holes 111 at two ends of the barrier element. The tightening belt 14 (or an elastic band) also can be used to position the barrier element on the body surface during the ultrasound focusing treatment and to protect the body surface from being burned by heat from the barrier element after reflecting or absorbing the ultrasound waves.

Figure 7A:
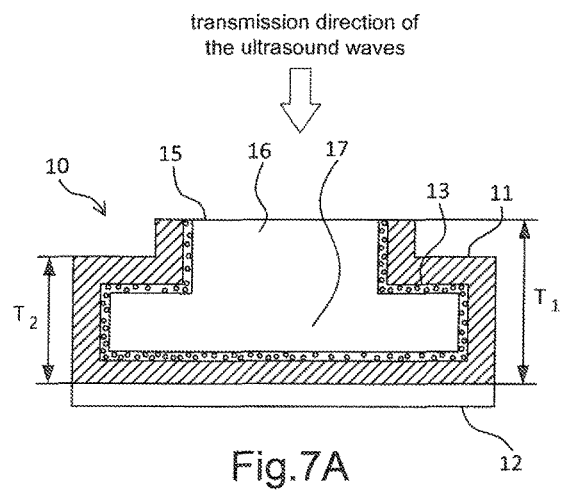
FIG. 7A is a transverse cross-sectional view of an ultrasound energy barrier according to a fifth embodiment of the present invention, similar to FIG. 2A.

Referring now to FIG. 7A, a transverse cross-sectional view of an ultrasound energy barrier according to a fifth embodiment of the present invention is illustrated and similar to the first embodiment, so that the fifth embodiment uses similar terms or numerals of the first embodiment. As shown, the difference of the fifth embodiment is that the ultrasound energy barrier 10 comprises: a barrier element and a positioning element, wherein the barrier element is a tubular reactive muffler which comprises an outer ultrasound reflection plate 11 and an inner ultrasound absorption plate 13 to reflect and absorb the ultrasound waves transmitted from an ultrasound probe during the ultrasound focusing treatment, respectively. The positioning element is an adhesive layer 12 adhered to a bottom surface of the outer ultrasound reflection plate 11.

Furthermore, the tubular reactive muffler (the barrier element) further comprises an opening 15, a channel 16 and a resonance cavity 17 in turn, wherein the resonance cavity 17 is communicated with the channel 16 and has no opening at the other side. An extension direction of the opening 15, the channel 16 and the resonance cavity 17 can be parallel to a transmission direction of the ultrasound waves. Thus, the ultrasound waves transmitted from the ultrasound probe can enter the channel 16 and the resonance cavity 17 from the opening 15 and will be attenuated by the reflection of the outer ultrasound reflection plate 11, the absorption of the inner ultrasound absorption plate 13 and the resonance of the resonance cavity 17, so that it can efficiently avoid energy accumulation in the ribs 51 during the high-intensity focused ultrasound (HIFU) treatment of the hepatic tumor 53, as shown in FIG. 5. In the embodiment, the thickness (T1, T2) of the tubular reactive muffler must be designed according to the foregoing equation, and the thickness (T1) from the opening 15 to the bottom surface of the outer ultrasound reflection plate 11 can be 2 or more times of the thickness (T2) from a stepped top surface of the outer ultrasound reflection plate 11 to the bottom surface thereof.

In alternative embodiment, the extension direction of the opening 15, the channel 16 and the resonance cavity 17 also can be perpendicular to a transmission direction of the ultrasound waves, in this case. FIG. 7D is a longitudinal cross-sectional view of the ultrasound energy barrier, and the ultrasound waves will pass through one side of the outer ultrasound reflection plate ii and the inner ultrasound absorption plate 13, and then enter the channel 16 and the resonance cavity 17, so as to be attenuated by the reflection of the outer ultrasound reflection plate 11, the absorption of the inner ultrasound absorption plate 13 and the resonance of the resonance cavity 17.

Figure 7B:
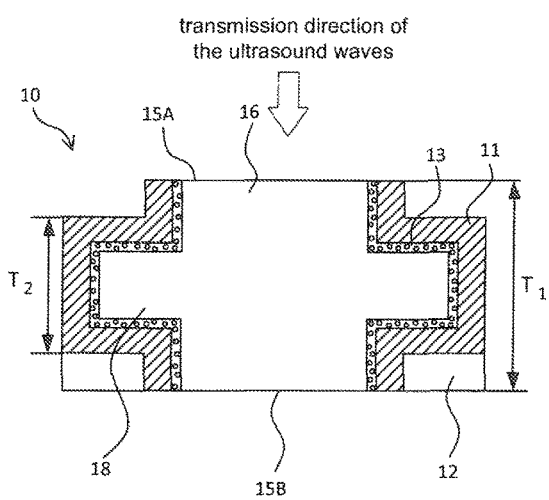
FIG. 7B is a transverse cross-sectional view of an ultrasound energy barrier according to a sixth embodiment of the present invention, similar to FIG. 7A.

Referring now to FIG. 7B, a transverse cross-sectional view of an ultrasound energy barrier according to a sixth embodiment of the present invention is illustrated and similar to the fifth embodiment, so that the sixth embodiment uses similar terms or numerals of the fifth embodiment. As shown, the difference of the sixth embodiment is that the ultrasound energy barrier 10 comprises: a barrier element and a positioning element, wherein the barrier element is a tubular acoustic filter which comprises an outer ultrasound reflection plate 11 and an inner ultrasound absorption plate 13 to reflect and absorb the ultrasound waves transmitted from an ultrasound probe during the ultrasound focusing treatment, respectively. The positioning element is a ring-type adhesive layer 12 adhered to a bottom surface of the outer ultrasound reflection plate 11.

Furthermore, the tubular reactive muffler (the barrier element) further comprises a first opening 15A, a channel 16 and a second opening 15B in turn, and the channel 16 has a middle expanded chamber 18 to attenuate the ultrasound waves, wherein the middle expanded chamber 18 is communicated with the channel 16 and formed on a middle portion of the channel 16. An extension direction of the first opening 15A, the channel 16 and the second opening 15B can be parallel to a transmission direction of the ultrasound waves. Thus, the ultrasound waves transmitted from the ultrasound probe can enter the channel 16 and the resonance cavity 17 from the first opening 15A and will be attenuated by the reflection of the outer ultrasound reflection plate 11, the absorption of the inner ultrasound absorption plate 13 and the attenuation of the middle expanded chamber 18, so that it can efficiently avoid energy accumulation in the ribs 51 during the high-intensity focused ultrasound (HIFU) treatment of the hepatic tumor 53, as shown in FIG. 5. In the embodiment, the thickness (T1, T2) of the tubular reactive muffler must be designed according to the foregoing equation, and the thickness (T1) from the first opening 15A to the second opening 15B can be 2 or more times of the thickness (T2) from a stepped top surface of the outer ultrasound reflection plate 11 to a stepped bottom surface thereof.

Figure 7C:
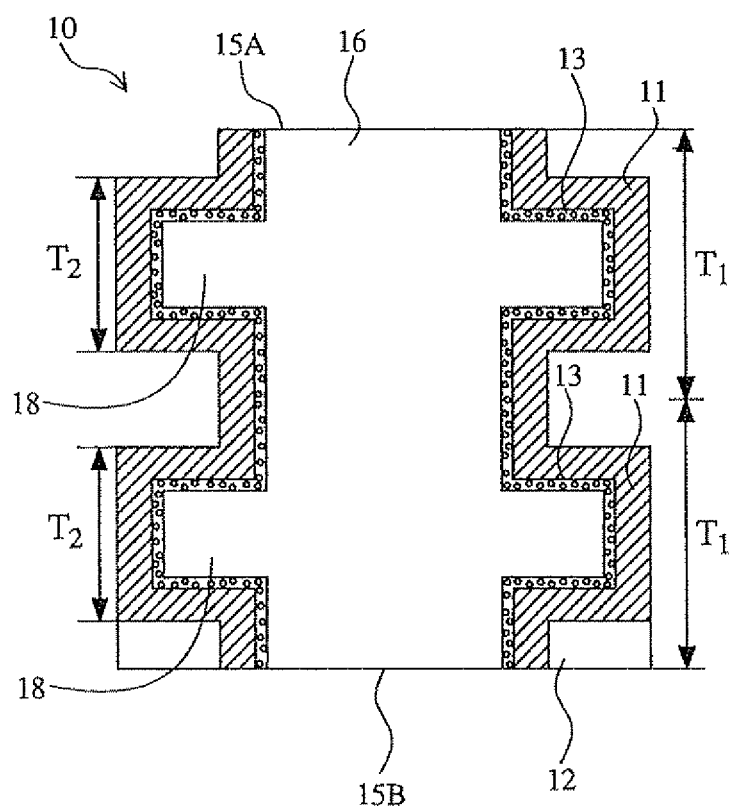
FIG. 7C is a transverse cross-sectional view of an ultrasound energy barrier according to a seventh embodiment of the present invention, similar to FIG. 7B.
Figure 7D:
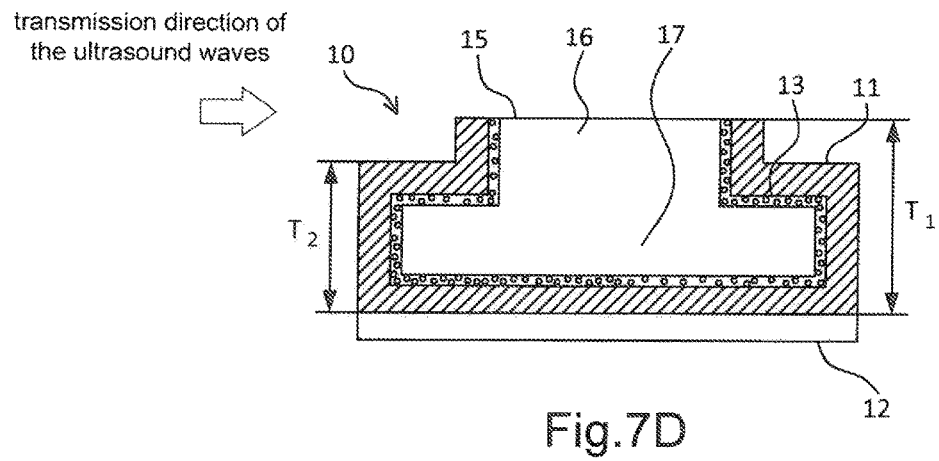
FIG. 7D is a longitudinal cross-sectional view of an ultrasound energy barrier according to an embodiment of the present invention, similar to FIG. 7A.
Figure 7E:
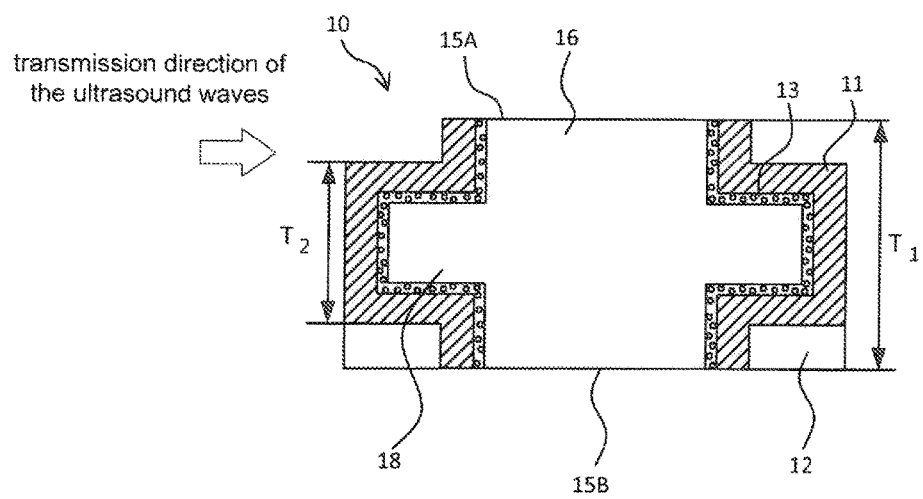
FIG. 7E is a longitudinal cross-sectional view of an ultrasound energy barrier according to an embodiment of the present invention, similar to FIG. 7B.

In alternative embodiment, the extension direction of the first opening 15A, the channel 16 and the second opening 15B also can be perpendicular to a transmission direction of the ultrasound waves, in this case, FIG. 7E is a longitudinal cross-sectional view of the ultrasound energy barrier, and the ultrasound waves will pass through one side of the outer ultrasound reflection plate 11 and the inner ultrasound absorption plate 13, and then enter the channel 16 and the middle expanded chamber 18, so as to be attenuated by the reflection of the outer ultrasound reflection plate 11, the absorption of the inner ultrasound absorption plate 13 and the attenuation of the middle expanded chamber 18.

Referring now to FIG. 7C, a transverse cross-sectional view of an ultrasound energy barrier according to a seventh embodiment of the present invention is illustrated and similar to the sixth embodiment, so that the seventh embodiment uses similar terms or numerals of the sixth embodiment. As shown, the difference of the seventh embodiment is that the barrier element of the ultrasound energy barrier 10 can be constructed by connecting two or more of the tubular acoustic filters with each other, wherein each of the tubular acoustic filters comprises an outer ultrasound reflection plate 11 and an inner ultrasound absorption plate 13, as shown in FIG. 7B, to reflect and absorb the ultrasound waves transmitted from an ultrasound probe during the ultrasound focusing treatment, respectively. The positioning element is a ring-type adhesive layer 12 adhered to a bottom-most surface of the outer ultrasound reflection plate 11.

Furthermore, if an external positioning tool can be used to hold and position the barrier element, the positioning element in the first to seventh embodiments (i.e. the adhesive layer 12 or the tightening belt 14) also can be selectively omitted to simplify the entire structure of the ultrasound energy barrier. Moreover, the type of the barrier element in the fourth to seventh embodiments can be selected from any type of the barrier element in the first to third embodiments, i.e. can select to only use an ultrasound reflection plate 11, only use an ultrasound absorption plate 13, or simultaneously use an ultrasound reflection plate 11 and an ultrasound absorption plate 13 based on actual desire.

As described above, in comparison with the traditional HIFU which is applied to a hepatic tumor and easily blocked by the ribs in the pathway of the ultrasound transmission to inevitably heat and burn the ribs, the ultrasound energy barrier of the present invention, as shown in FIGS. 1 to 7B, has a barrier element having an outline matched with the to-be-protected region for shielding the to-be-protected region, so as to reflect or absorb ultrasound waves/energy and thus avoid energy accumulation in the to-be-protected region during an ultrasound focusing treatment of a to-be-treated tumor. Furthermore, the thickness of the barrier element along a transmission direction of the ultrasound waves can be designed to cause that the barrier element has a transmission coefficient equal to 1. Thus, the barrier element can block a portion of the ultrasound waves to protect ribs from being heated and burned, while other portion of the ultrasound waves still can transmit and pass through a space between each two of adjacent barrier elements to be focused on a hepatic tumor behind the ribs. Moreover, the barrier element is made of plastic deformation material or elastic deformation material, so that the barrier element can be temporarily, permanently or elastically deformed to have a curved configuration which is advantageous to substantially match with a profile of the body surface of the animal. In addition, the ultrasound energy barrier has a positioning element, such as an adhesive layer, a tightening belt or an elastic band, which is used to position the barrier element on the body surface during the ultrasound focusing treatment, wherein the adhesive layer is preferably made of thermal insulation material to protect the body surface from being burned by heat from the barrier element.

The present invention has been described with a preferred embodiment thereof and it is understood that many changes and modifications to the described embodiment can be carried out without departing from the scope and the spirit of the invention that is intended to be limited only by the appended claims.

What is claimed is:

1. An ultrasound barrier system, comprising:
a barrier element for attaching to a surface of a to-be-protected region, wherein the barrier element has an outline for matching with the to-be-protected region to thus shield the to-be-protected region, so as to avoid energy accumulation in the to-be-protected region;
a positioning element for positioning the barrier element on the surface of the to-be-protected region; and
an ultrasound probe configured to generate ultrasound waves,
wherein the barrier element comprises one ultrasound reflection plate and one ultrasound absorption plate configured to respectively reflect and absorb ultrasound waves transmitted from the ultrasound probe, and the ultrasound reflection plate and the ultrasound absorption plate are attached to each other, and
wherein the barrier element further comprises an opening, a channel, and a resonance cavity, which are formed by deforming the ultrasound reflection plate and the ultrasound absorption plate, and the resonance cavity is in communication with the channel.

2. The ultrasound energy barrier system according to claim 1, wherein the ultrasound absorption plate is made of ultrasound absorption material, wherein a diameter of pores or perforation holes is smaller than ½ of a wavelength of the ultrasound waves.

3. The ultrasound energy barrier system according to claim 1, wherein the opening, the channel, and the resonance cavity are arranged along a direction that is parallel to a transmission direction of the ultrasound waves.

4. The ultrasound energy barrier system according to claim 1, wherein the opening, the channel, and the resonance cavity are arranged along a direction that is perpendicular to a transmission direction of the ultrasound waves.

5. The ultrasound energy barrier system according to claim 1, wherein the barrier element is made of a plastic deformation material or an elastic deformation material.

6. The ultrasound energy barrier system according to claim 1, wherein the positioning element is an adhesive layer which is made of thermal insulation material and adhered to a surface of the barrier element.

7. The ultrasound energy barrier system according to claim 1, wherein the positioning element is a tightening belt or an elastic band, which is made of thermal insulation material and has two tying ends tied on two ends of the barrier element.

8. The ultrasound energy barrier system according to claim 1, wherein the frequency of the ultrasound waves transmitted from the ultrasound probe is 0.5-5 MHz.

9. An ultrasound energy barrier system, comprising:
a barrier element for attaching to a surface of a to-be-protected region, wherein the barrier element has an outline for matching with the to-be-protected region to thus shield the to-be-protected region, so as to avoid energy accumulation in the to-be-protected region; and
an ultrasound probe configured to generate ultrasound waves,
wherein the barrier element comprises one ultrasound reflection plate and one ultrasound absorption plate configured to respectively reflect and absorb ultrasound waves transmitted from the ultrasound probe, and the ultrasound reflection plate and the ultrasound absorption plate are attached to each other;
wherein the barrier element further comprises a first opening, a channel, and a second opening, which are formed by deforming the ultrasound reflection plate and the ultrasound absorption plate, and a middle portion of the channel has an expanded chamber.

10. The ultrasound energy barrier system according to claim 9, wherein the first opening, the channel, and the second opening are arranged along a direction that is parallel to a transmission direction of the ultrasound waves.

11. The ultrasound energy barrier system according to claim 9, wherein the first opening, the channel, and the second opening are arranged along a direction that is perpendicular to a transmission direction of the ultrasound waves.

* * * * *